(12) United States Patent
Schwartz et al.

(10) Patent No.: US 8,318,203 B2
(45) Date of Patent: Nov. 27, 2012

(54) FORM OF ADMINISTRATION OF RACECADOTRIL

(75) Inventors: Jean-Charles Schwartz, Paris (FR); Jeanne-Marie Lecomte, Paris (FR)

(73) Assignee: Bioprojet, Paris (FR)

( * ) Notice: Subject to any disclaimer, the term of this patent is extended or adjusted under 35 U.S.C. 154(b) by 119 days.

(21) Appl. No.: 12/300,465

(22) PCT Filed: May 14, 2007

(86) PCT No.: PCT/FR2007/000814
§ 371 (c)(1),
(2), (4) Date: Nov. 12, 2008

(87) PCT Pub. No.: WO2007/132091
PCT Pub. Date: Nov. 22, 2007

(65) Prior Publication Data
US 2009/0186084 A1   Jul. 23, 2009

(30) Foreign Application Priority Data
May 15, 2006   (FR) .................................... 06 04302

(51) Int. Cl.
*A61K 9/28* (2006.01)
(52) U.S. Cl. ......................... 424/474; 424/464; 424/465
(58) Field of Classification Search ........................ None
See application file for complete search history.

(56) References Cited

U.S. PATENT DOCUMENTS

| 4,401,677 | A * | 8/1983 | Greenberg et al. ........... 514/562 |
| 6,919,093 | B2 | 7/2005 | Lecomte et al. |
| 2004/0115258 | A1 * | 6/2004 | Stroppolo et al. ........... 424/465 |
| 2004/0253305 | A1 * | 12/2004 | Luner et al. .................. 424/451 |
| 2005/0027012 | A1 * | 2/2005 | Kohlrausch ................... 514/649 |
| 2006/0051417 | A1 * | 3/2006 | Friedl et al. .................. 424/468 |
| 2007/0254050 | A1 * | 11/2007 | Quart et al. .................. 424/725 |
| 2007/0275993 | A1 | 11/2007 | Schwartz et al. |

FOREIGN PATENT DOCUMENTS

| WO | WO 01/97803 | 12/2001 |
| WO | WO 2005/079850 | 9/2005 |

OTHER PUBLICATIONS

Wang et al "A blind, randomized comparison of racecadotril and loperamide for stopping acute diarrhea in adults", World Journal of Gastroenterology, 11(10), p. 1540-1543.*
Qin et al; "Relative bioavailability of racecadotril orally disintgerating tablets in healthy volunteers"; Chinese Journal of New Drugs, vol. 15, No. 19 (Jan. 4, 2006) p. 1691-1693 and 1643.*
Translation of Qin et al; "Relative bioavailability of racecadotril orally disintgerating tablets in healthy volunteers"; Chinese Journal of New Drugs, vol. 15, No. 19 (Jan. 4, 2006) p. 1691-1693.*
"Racecadotril" Wikipedia (http://en.wikipedia.org/wiki/Racecadotril) pp. 1-2.*
Sankar, D. Gowri, et al, "Spectrophotometric determination of famciclovir and racecadotril", Asian Journal of Chemistry, vol. 17, No. 3, 2005, pp. 2043-2045.
Schwartz, J.C. "Symposium on the treatment of diarrhoeal disease—Racecadotril: a new approach to the treatment of diarrhoea", 2000, pp. 75-79, International Journal of Antimicrobial Agents 14.
Lecomte, J.M., "Symposium on the treatment of diarrhoeal disease—An overview of clinical studies with racecadotril in adults", 2000, pp. 81-87, International Journal of Antimicrobial Agents 14.
Matheson et al, "Racecadotril", Apr. 2000, pp. 829-835, vol. 59—No. 4, Drugs 2000.
European Search Report (In French) regarding EP 07 731 453.2 Jun. 2012.
Summary of Official Action in Egyptian Equivalent application Jun. 2012.
Nichol G M et al, "Effect of Neutral Endopeptidase Inhibitor on Airway Function and Bronchial Responsiveness in Asthmatic Subjects", European Journal of Clinical Pharmacology, Springer Verlag, DE, vol. 42, No. 5, Jan. 1, 1992, pp. 491-494, XP008073220.
Saliba F et al, "Pathophysiology and therapy of irinotecan-induced delayed-onset diarrhea in patients with advanced colorectal cancer: A prospective assessment", Journal of Clinical Oncology: Official Journal of the American Society of Clinical Oncology, United States, vol. 16, No. 8, Aug. 1998, pp. 2745-2751, XP008150349.
Wasterhuis, Johan A. et al, "Multivariate modeling of the tablet manufacturing process with wet granulation for tablet optimization and in-process control", International Journal of Pharmaceutics vol. 156, No. 1, pp. 109-117, Oct. 1997.

* cited by examiner

*Primary Examiner* — Bethany Barham
(74) *Attorney, Agent, or Firm* — B. Aaron Schulman, Esq.; Stites & Harbison PLLC

(57) ABSTRACT

The present invention relates to a new racecadotril formulation in the form of tablets, the preparation process thereof and the use thereof to treat diarrhoea.

13 Claims, No Drawings

FORM OF ADMINISTRATION OF RACECADOTRIL

The present invention relates to a new racecadotril formulation, the process for the preparation thereof, and the use thereof in the treatment of diarrhoea.

Racecadotril or acetorphan is the racemic compound of formula benzyl (RS)-2-[[2-[(acetylsulphanyl)methyl]-3-phenylpropanoyl]amino]acetate.

It is a powerful enkephalinase inhibitor, exhibiting an original intestinal antisecretary action, by protecting endogenous enkephalines against the degradation thereof. By improving the biological activity of these neuropeptides at the delta opiate receptors, racecadotril reduces the hydroelectric flows in the intestinal lumen, which flows are otherwise increased in diarrhoeal diseases of various origins. In a highly beneficial manner, the powerful antidiarrhoeal activity of racecadotril is selective in that the intestinal hypersecretion (or reduced electrolyte reabsorption) which characterises diarrhoea and is responsible for severe states of dehydration is greatly reduced without altering the transit (Matheson A. J. & Noble S., *Drugs* 2000, 59, 829; Schwartz J.-C., *Int. Antimicrob. Agents,* 2000, 14, 81). This model, unique amongst the antidiarrhoeals, contributes to the particularly beneficial properties of racecadotril, as has already been shown in numerous clinical trials and in the post-marketing study, after use by millions of patients (Lecomte et al., Int. *J. Antimicrob. Agents,* 2000, 14, 81).

In clinical trials as well as in standard practice, racecadotril is generally administered in 100 mg capsules, taken three times a day in order to ensure complete inhibition of the targeted peptidase throughout the day without interruption. Although highly effective, this administration scheme does not promote observance of the treatment by the patient, in particular in patients who do not wish to interrupt their habitual professional routine. For this reason, administration twice a day (b.i.d.) is preferable.

It is therefore desirable to improve observance of the treatment by means of a racecadotril formulation allowing administration twice a day.

Nevertheless, because the half-life of racecadotrilate, the biologically active metabolite of the pro-drug racecadotril, is only three to four hours, it is necessary to increase the bioavailability of the active ingredient to allow a 24-hour enkephalinase inhibition.

The bioavailability may be modulated by means of a different formulation. Nevertheless, tablets are considered to be inferior to capsules, capsules generally being considered the formulation which allows the highest oral bioavailability.

Contrary to all expectations and in accordance with one of the objects of the present invention, the inventors have surprisingly found that the formulation of racecadotril in the form of tablets enables a higher bioavailability of the active ingredient, thus allowing administration twice a day.

This formulation therefore enables a 24-hour inhibition of the target enzyme and an improved clinical effectiveness as compared with the conventionally used capsule which is administered three times a day.

According to a first subject-matter, the present invention relates to a racecadotril tablet.

A priori, racecadotril seems particularly inappropriate for the preparation of tablets. In fact, the crystalline form thereof, consisting of long needles, and the very low solubility thereof in water make direct compression thereof difficult. Moreover, large quantities of racecadotril are necessary, whereas it is generally desirable to obtain a tablet of a small size (between 10 and 15 mm in diameter at most) in order to increase the acceptability thereof and improve the observance of the treatment by the patient. Furthermore, racecadotril is insoluble in water and this makes a rapid release of the molecule by disintegration of the tablet more difficult. Finally, racecadotril has a bitter flavour and an unpleasant aroma due to the presence of sulphur in the molecule; it is therefore necessary to make available a tablet which conceals the flavour and the aroma.

Racecadotril therefore exhibits particularly unfavourable properties for formulation in the form of tablets which can be produced easily on an industrial scale and which are fully acceptable to and effective in patients. Despite these disadvantages, the present inventors have found that some tablets containing racecadotril meet these various criteria.

In accordance with a first feature, the racecadotril tablets according to the invention allow administration twice a day (b.i.d).

In accordance with another feature, the racecadotril tablets according to the invention allow the administration of a dose of racecadotril of between 170 and 180 mg per tablet, preferably approximately 175 mg per tablet.

In accordance with another feature, the racecadotril tablets according to the invention comprise from 20% to 50% by weight of racecadotril.

Preferably, said tablets consist of a coated core, with the core containing racecadotril. The tablet has a weight of between 350 and 600 mg.

Said core contains, in addition to racecadotril, various conventionally used excipients, such as:

optionally one or more fillers: for example lactose monohydrate, which allows the tablet to be prepared by wet granulation, in particular lactose of the "200 mesh" or "110 mesh" type, which exhibits a defined particle size distribution, or even lactose monohydrate of the "Flowlac®" type in the form of powder dried out by vaporisation; another possible filler is microcrystalline cellulose (for example of the Avicel® PH102 type). Mannitol or sorbitol may equally be used. As a filler, lactose monohydrate of the "200 mesh" or "110 mesh" type, in particular "110 mesh", or of the "Flowlac®" type is preferred, or even microcrystalline cellulose (for example of the Avicel® PH102 type).

optionally one or more binders such as hydroxypropylcellulose or polyvidone; it is preferable to use hydroxypropylcellulose, for example of the Klucel® EF type, in the granules and the external phase;

optionally one or more disintegrants, such as carmellose calcium, cornflour or pre-gelatinised starch; carmellose calcium in the granules and the external phase and/or pre-gelatinised starch in the external phase are preferable;

optionally one or more lubricants, such as magnesium stearate, for preventing the mass of compacted powder from sticking to the equipment; magnesium stearate is most particularly preferred in the external phase.

The coating of the core consists of one or more conventionally used excipients, in such a way as to mask the sulphurous aroma and bitterness of the active ingredient. The coating formulation may include viscosifying agents, such as polyvinyl alcohol; opacifiers, such as titanium dioxide; hydrophilic plasticizers, such as molecules of the Macrogol type (for example Macrogol 3350) which improve the flexibility of the film; and colouring opacifying agents such as talc.

To prepare the coating, these various coating ingredients may be dispersed in purified water. Particularly advantageously, the ready-to-use mixture Opadry® may be used, comprising:
- 40% polyvinyl alcohol,
- 25% titanium dioxide,
- 20.2% Macrogol 3350, and
- 14.8% talc.

In accordance with a preferred feature, the racecadotril tablets according to the invention have a core of the following composition:
- 20 to 50% racecadotril;
- 25 to 50% filler(s);
- 9 to 25% disintegrant(s);
- 2 to 10% binding agent(s);
- 0.5 to 5% lubricant(s);

and more preferably:
- 20 to 50% racecadotril;
- 20 to 40% lactose monohydrate;
- 7 to 15% carmellose calcium;
- 2 to 10% hyroxypropylcellulose;
- 5 to 10% microcrystalline cellulose;
- 2 to 10% pre-gelatinised starch;
- 0.5 to 5% magnesium stearate.

Even more preferably, the cores of the tablets according to the invention are of the following composition:
- 175 mg racecadotril;
- 144.1 mg lactose monohydrate;
- 41 mg carmellose calcium;
- 18 mg hydroxypropylcellulose;
- 32.5 mg microcrystalline cellulose;
- 25 mg pre-gelatinised starch;
- 4.4 mg magnesium stearate.

In accordance with a further subject-matter, the present invention also relates to the preparation process for a racecadotril tablet according to the invention, comprising the steps of:
1) preparing the core containing the racecadotril, then
2) coating said core.

The first step involves:
(i) granulation;
(ii) drying out the obtained granules;
(iii) adding and mixing the external phase; and
(iv) compressing the final mixture.

The granulation is carried out by the granulation method known as wet granulation. The granulation step involves:
a) preparing an internal phase mixture;
b) adding and mixing granulation liquid into the internal phase.

Apart from the racecadotril, the internal phase generally consists of filler(s) and disintegrant(s). Preferably, the internal phase consists of racecadotril, lactose monohydrate, carmellose calcium and/or optionally cornflour.

The granulation liquid contains the binding agent, preferably hydroxypropylcellulose, and water.

The external phase generally constitutes lubricant(s), filler(s), disintegrant(s) and/or binding agent(s). Preferably, the external phase constitutes lactose monohydrate, microcrystalline cellulose, carmellose calcium and magnesium stearate, and optionally pre-gelatinised starch and hydroxypropylcellulose.

Preferably, the ingredients of the internal phase are placed in a stirrer of the type conventionally used, for a sufficient duration and at a sufficient speed to allow a homogeneous mixture to be obtained. This may in particular be a stirrer of the Erweka or Colette type. The mixing times are of between 1 and 20 minutes, at rotation speeds of between 150 and 500 rpm, preferably approximately 3 minutes at approximately 200 rpm or approximately 10 minutes at approximately 60 rpm.

The granulation liquid is prepared by means of a propeller-type stirrer by dispersing the binding agent in the water until a clear solution is obtained. Generally, stirring continues for 10 to 30 minutes, and the speeds are of between 100 and 1000 rpm, preferably approximately 15 minutes at 500 rpm. The liquid is subsequently added to the previous mixture with stirring; purified water may be added.

The drying step is carried out with a fluidised bed (of the Glatt type for example) or in an oven at a temperature such that a loss of weight from drying of 1% to 3%, preferably less than 1.5%, is obtained. Generally, drying for approximately 20 hours at 400 is appropriate. The dying time is set in such way as to allow the granules to be sized while limiting the number of unclassifiable particles obtained. Generally, a residual humidity of 1% allows for satisfactory results. The dry granules obtained are generally sized on a 0.8 mm oscillating sieve, such as the sieve of the Frewitt type.

The ingredients of the external phase are added to the granules and mixed in a stirrer of the type conventionally used for a sufficient duration and at a sufficient speed to allow a homogenous mixture to be obtained. This may in particular be a stirrer of the Turbula, Roehn or Soneco type. The mixing durations are of between 5 and 30 minutes, at speeds of rotation of between 10 and 100 rpm, preferably approximately 15 minutes at approximately 30 rpm or approximately 5 minutes at approximately 10 rpm.

Preferably, the magnesium stearate is sieved in advance on a 0.315 mm sieve; it is added only after mixing the other ingredients of the external phase with the granules, and then the whole is mixed for approximately 1 to 5 minutes.

To compress the final mixture, equipment parameters such as the mass and the compression force as well as the compression speed may be adjusted in such a way as to obtain the tablets desired. Compression may be carried out on any type of machine for the preparation of tablets, in particular apparatuses of the Frogerais or Courtoy R190 type, equipped with stamps of the 11R11 or 12R12 type. The hardness is set to approximately 80 N.

The cores are then transferred onto a coating platform (for example of the Accela Cota type) and heated (preferably approximately 40° C.) during the coating by pulverisation of the coating suspension disclosed above. Pulverisation is continued up to a weight gain of approximately 10 mg.

In accordance with another subject-matter, the present invention also relates to the use of racecadotril for the preparation of a tablet for the treatment of diarrhoea for administration twice a day, preferably allowing the administration of 175 mg of racecadotril per tablet.

Said tablet is as defined in accordance with the tablets according to the invention disclosed above.

The following examples are provided as a non-limiting illustration of the present invention.

EXAMPLE 1

The racecadotril tablets were prepared with the following composition:

| Internal phase | |
|---|---|
| Racecadotril | 175 |
| Lactose monohydrate | 100 |
| Carmellose calcium | 35 |

| Granulation liquid | |
| --- | --- |
| Hydroxypropylcellulose | 12 |
| Purified water | sq |

| External phase | |
| --- | --- |
| Lactose monohydrate | 44 |
| Microcrystalline cellulose | 32.5 |
| Carmellose calcium | 6 |
| Magnesium stearate | 2.5 |
| Pre-gelatinised starch | 25 |
| Hydroxylpropylcellulose | 6 |

| Coating | |
| --- | --- |
| Opadry ® White | 10 |
| Purified water | sq |

The quantities indicated above are given in mg.

Alternatively:

175 mg racecadotril;

144.1 mg lactose monohydrate;

41 mg carmellose calcium;

18 mg hydroxypropylcellulose;

32.5 mg microcrystalline cellulose;

25 mg pre-gelatinised starch;

4.4 mg magnesium stearate;

10 mg of coating (Opadry® white)

EXAMPLE 2

The tablets from example 1 were prepared in the following manner: the ingredients of the internal phase were mixed in a stirrer of the Erweka type for 3 minutes at 180 rpm. A 7.5% (weight/volume) hydroxypropylcellulose solution was prepared in water in order to improve the bonding properties. The granulation liquid obtained was added to the powder mixture obtained previously, with stirring at 180 rpm. In accordance with the feature relating to the granules, the granulation was completed with purified water.

The granules were dried in an oven at 40° C. until a loss of 1 to 3% was obtained and the dried granules were sized on a 0.8 mm sieve.

The ingredients of the external phase, with the exception of the magnesium stearate, i.e. the lactose monohydrate of the Flowlac® type, the microcrystalline cellulose of the Avicel® PH 102 type and the carmellose calcium, were added to the granules and mixed with a stirrer of the Turbula type for 15 minutes. The magnesium stearate, sieved at 0.315 mm, was added afterwards then stirred for 5 minutes.

The final mixture was compressed on a tabletting machine equipped with 12R12 stamps.

Finally, a coating was prepared with the Opadry® White mixture consisting of polyvinyl alcohol, titanium dioxide, Macrogol 3350 and talc, in order to suppress the aroma and the flavour of the racecadotril.

EXAMPLE 3

Bioavailability Compared In Vivo in Healthy Human Volunteers

The double-blind crossover trial was carried out on eight healthy volunteers in order to compare the relative bioavailability of the new formulation in the form of 175 mg racecadotril tablets with the control formulation (100 mg racecadotril capsules).

The tablets were administered twice a day, morning and evening, and the capsules three times, morning, noon and evening, in accordance with current recommendations. Consequently, patients received the tablets and capsules at a total dosage of 350 mg per 24 hours and 300 mg per 24 hours respectively. The bioavailability was evaluated by measuring the levels of racecadotrilate, the active metabolite of racecadotril, in the blood serum, at different points over a 24-hour period. For this purpose, a test confirmed as highly precise and highly sensitive, based on HPLC/MS evaluation of racecadotrilate of pre-column derivatisation, was used. Numerous observations indicated that surprisingly, the formulation in the form of tablets exhibits a superior bioavailability profile, and specifically:

- the average Tmax values, i.e. the period required to observe the peak in blood levels after injection, were 1.15 hours and 1.66 hours for the tablets and the capsules respectively. This is surprising insofar as capsules generally allow the active ingredient to be made bioavailable more rapidly.
- the total AUC values (area under curve) over 24 hours, expressed in nM.h, were 4669 and 2552 for the tablets and capsules respectively, corresponding to areas under the curve of 13.34 and 8.50 per mg respectively. This indicates that the racecadotril was more highly available by 56% when formulated in the form of tablets than in the standard capsule conventionally used.
- the improved bioavailability of the tablets thus allowed administration of the capsules twice a day by comparison with the current administration three times a day. Consequently, the serum concentrations of racecadotrilate 12 hours after administration of the tablets (and immediately before the following administration) were still sufficiently high (approximately 4 nM) to inhibit the targeted enkephalinase enzyme, which exhibits a Ki value of 2 nM for the active metabolite.

EXAMPLE 4

Clinical Effect Compared in Severe Diarrhoea

This comparison was carried out in a double-blind, double-placebo multicentre study on 221 ambulatory adult subjects suffering from acute diarrhoea. The patients received either a 175 mg tablet twice a day (110 patients) or the conventional 100 mg capsule three times a day (111 patients). The criteria for inclusion were the sudden appearance of acute diarrhoea, defined by the occurrence of at least three liquid or semi-solid bowel movements during the last 24 hours and over a period not exceeding 72 hours. The criteria for non-inclusion included the presence of blood or pus in the bowel movements as well as chronic diarrhoea.

The main evaluation criterion was the number of diarrhoeal bowel movements which had taken place between the start of treatment and recovery, or day 7 if the patients had not been cured. Additional criteria included the percentage recovery upon the final visit, the duration of the diarrhoea, the development of associated symptoms, the need for additional treatment, and the percentage reduction in the diarrhoea.

The treatments began on the first visit; the patients were also observed on day 3 and on day 7 and had to fill in a diary describing their symptoms. The average number of diarrhoeal bowel movements before recovery, i.e. the main criterion of effectiveness, was 4±3.8 for the tablets versus 6.2±11.2 for the capsules. The comparison of these values by means of a square root transformation and adjustment of the severity of the diarrhoea to the base line showed that the treatment twice a day with tablets was, surprisingly, significantly superior to the conventional administration three times a day of the capsule ($P \leq 0.0001$). The secondary criteria showed the same tendencies and the only unfavourable occurrences were minor, generally connected to the pathology rather than to the treatment.

More specifically, the analysis of the duration of the diarrhoea showed that the administration of tablets twice a day allowed the duration of the diarrhoea to be reduced significantly by comparison with the administration of capsules three times a day (13.73 h vs. 17.48 h; p=0.0238).

It may therefore be concluded that the new treatment is more effective than the conventional treatment and exhibits the advantages of easier administration and an improvement in the observance of the treatment, in particular in patients who do not wish to interrupt their daily routine.

The invention claimed is:

1. A racecadotril tablet comprising a coated core, said core containing racecadotril, wherein said core comprises by weight:
   20 to 50% racecadotril;
   25 to 50% filler(s);
   9 to 25% disintegrant(s);
   2 to 10% binding agent(s);
   0.5 to 5% lubricant(s).

2. A tablet according to claim 1, wherein said tablet contains between 170 and 180 mg of racecadotril per tablet.

3. A tablet according to claim 1, containing approximately 175 mg of racecadotril per tablet.

4. A tablet according to claim 1, wherein the filler or fillers are selected from lactose monohydrate, microcrystalline cellulose, mannitol and sorbitol.

5. A tablet according to claim 1, wherein the binding agent or agents are selected from hydroxypropylcellulose and polyvidone.

6. A tablet according to claim 1, wherein the coating consists of one or more excipients selected from viscosifying agents, opacifiers, hydrophilic plasticizers and coloring opacifiying agents.

7. A tablet according to claim 1, wherein the core comprises, by weight:
   20 to 50% racecadotril;
   20 to 40% lactose monohydrate;
   7 to 15% carmellose calcium;
   2 to 10% hyroxypropylcellulose;
   5 to 10% microcrystalline cellulose;
   2 to 10% pre-gelatinised starch;
   0.5 to 5% magnesium stearate.

8. A tablet according to claim 1, wherein the core comprises:
   175 mg racecadotril;
   144.1 mg lactose monohydrate;
   41 mg carmellose calcium;
   18 mg hydroxypropylcellulose;
   32.5 mg microcrystalline cellulose;
   25 mg pre-gelatinised starch;
   4.4 mg magnesium stearate.

9. A process for preparing a racecadotril tablet according to claim 1, comprising the steps of:
   1) preparing of the core containing the racecadotril, then 2) coating said core.

10. A process according to claim 9, wherein step 1) involves:
    (i) granulation;
    (ii) drying out the obtained granules;
    (iii) adding and mixing the external phase; and
    (iv) compressing the final mixture.

11. Method for the treatment of diarrhoea comprising the administration twice a day of a racecadotril tablet according to claim 1.

12. Method for the treatment of diarrhoea according to claim 11, wherein the tablet allows the administration of 175 mg of racecadotril.

13. A tablet according to claim 1, wherein:
    the filler or fillers are selected from the group consisting of lactose monohydrate, microcrystalline cellulose, mannitol and sorbitiol; 20 to 50% racecadotril;
    the binding agent or agents are selected from the group consisting of hydroxypropylcellulose and polyvidone; and
    the disintegrant or disintegrates are selected from the group consisting of carmellose calcium, corn flour and pre-gelatinized starch.

* * * * *